United States Patent
Gjerde

(10) Patent No.: US 8,143,071 B2
(45) Date of Patent: Mar. 27, 2012

(54) METHOD AND DEVICE FOR EXTRACTING AN ANALYTE

(75) Inventor: Douglas T. Gjerde, Saratoga, CA (US)

(73) Assignee: PhyNexus, Inc., San Jose, CA (US)

( * ) Notice: Subject to any disclaimer, the term of this patent is extended or adjusted under 35 U.S.C. 154(b) by 375 days.

(21) Appl. No.: 12/004,726

(22) Filed: Dec. 21, 2007

(65) Prior Publication Data

US 2008/0214794 A1 Sep. 4, 2008

Related U.S. Application Data

(60) Provisional application No. 60/876,911, filed on Dec. 21, 2006.

(51) Int. Cl.
*G01N 33/543* (2006.01)

(52) U.S. Cl. ............ 436/518; 210/198.2; 210/635; 210/656; 436/6; 436/501

(58) Field of Classification Search .............. None
See application file for complete search history.

(56) References Cited

U.S. PATENT DOCUMENTS

| | | | | |
|---|---|---|---|---|
| 5,573,920 A | * | 11/1996 | Randle | 435/7.9 |
| 2004/0142488 A1 | * | 7/2004 | Gjerde et al. | 436/178 |
| 2007/0065343 A1 | * | 3/2007 | Srinivasan et al. | 422/70 |

* cited by examiner

*Primary Examiner* — N Yang
(74) *Attorney, Agent, or Firm* — Sue S. Kalman

(57) ABSTRACT

The invention provides columns and methods for the purification and concentration of an analyte (e.g., a biological macromolecule, such as a peptide, protein or nucleic acid) from a sample solution. The columns typically include a bed of extraction medium positioned in the column between two frits. In some embodiments, the extraction columns employ modified pipette tips as column bodies. The invention also provides methods for purifying and concentrating multiple analytes simultaneously.

15 Claims, 6 Drawing Sheets

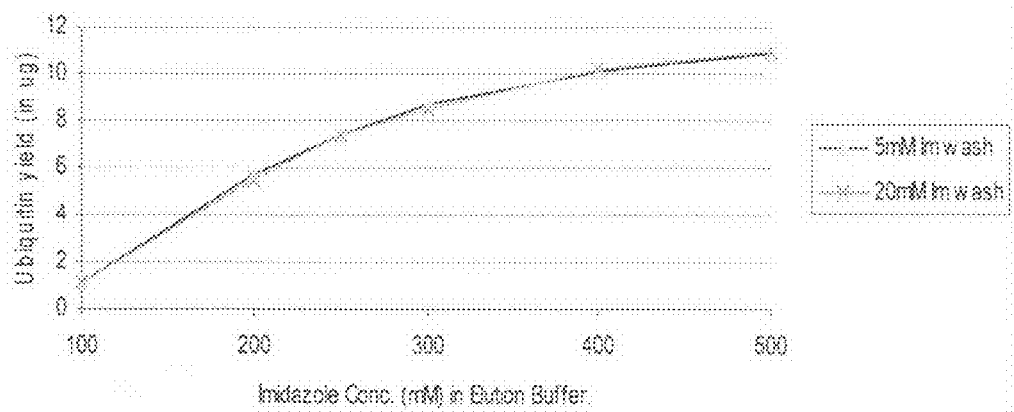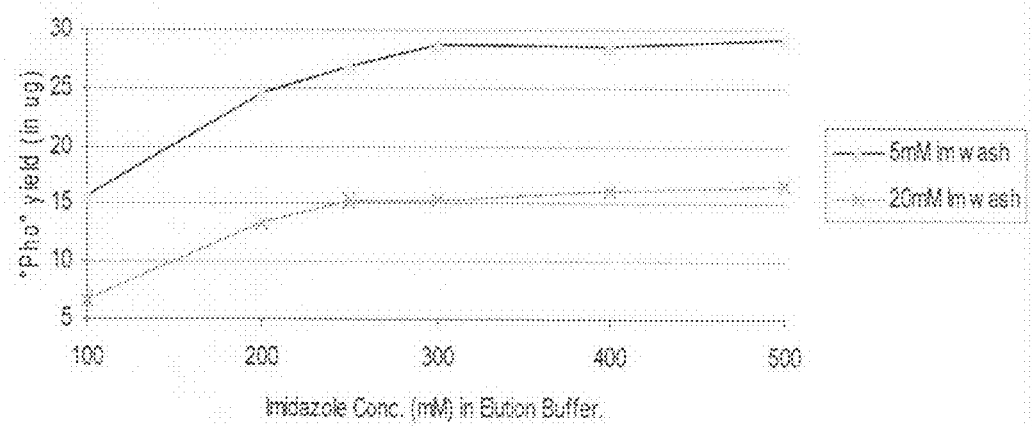
Figure 3

FIG. 5: Protein yield versus capture flow rate and number of capture cycles.

METHOD AND DEVICE FOR EXTRACTING AN ANALYTE

CROSS REFERENCE TO RELATED APPLICATIONS

This application claims priority to and benefit of U.S. Provisional Patent Application No. 60/876,911 filed Dec. 21, 2006, the disclosure of which is incorporated herein by reference in their entirety for all purposes.

FIELD OF THE INVENTION

This invention relates to methods and devices for extracting an analyte from a sample solution. The analytes can include biomolecules, particularly biological macromolecules such as proteins and peptides. The devices and methods of this invention are particularly useful in proteomics for sample preparation and analysis with analytical technologies employing x-ray crystallography, cryo-electron microscopy (cryo-EM), nuclear magnetic resonance and a variety of other instrumentation and assays.

BACKGROUND OF THE INVENTION

Solid phase extraction is a powerful technology for purifying and concentrating analytes, including biomolecules. For example, it is one of the primary tools used for preparing protein samples prior to analysis by any of a variety of analytical techniques, including mass spectrometry, cryo-EM, nuclear magnetic resonance, x-ray crystallography, cell based assays, and the like. With these techniques, typically only a small volume of highly-concentrated sample is required, however, it is often critical that interfering contaminants be removed from the sample. Thus, sample preparation methods are needed that permit the purification and concentration of samples. Both of these parameters are particularly important for determining structure and function of the biological material such as proteins, polypeptides, and other materials.

Traditionally, high concentrations of a desired analyte are obtained from chromatography columns using the heart-cut method. This involves collecting fractions and determining analyte concentration within each fraction. For a protein analyte, concentration determination can require a spectrophotometer. After the concentration of each fraction is determined, those fractions that contain the highest concentration of analyte are retained. This process is time-consuming, labor-intensive and equipment-intensive and cannot be automated. Therefore, better methods are needed to obtain highly concentrated, pure material for a variety of analytical processes.

SUMMARY OF THE INVENTION

The subject invention involves a two-step process for obtaining a very high concentration of an analyte from a sample solution. The invention has multiple benefits over existing methods. The process is simpler and does not require fraction collection and monitoring with a detector such as a spectrophotometer. Since multiple fractions are not collected, less glassware and disposable laboratory ware is needed. In addition, the invention has the benefit of routinely yielding higher analyte concentrations than traditional methods such as heart cut. Using this method, it is possible to maintain the structure of protein analytes, keeping them active. Finally, the method can be automated, an advantage not easily done with existing methods.

The invention can be practiced using extraction columns, and particularly pipette-tip columns. PhyTip columns (PhyNexus, Inc.) are particularly well-suited for use with the methods of the invention. During the first step in the process, the analyte is purified using an extraction column such as a pipette-tip column. Purification conditions are chosen so that the analyte is uniform in identity. The second step of the process involves concentrating the analyte. This is accomplished by using a smaller or lower capacity pipette-tip column than the first column. The column is loaded to as high a density as possible and the analyte is eluted with as small a volume as possible to produce a high concentration of very pure analyte.

This process, and the related devices and reagents, will be of particular interest to the life scientist, since they provide a powerful technology for purifying, concentrating and analyzing biomolecules and other analytes of interest. However, the methods, devices and reagents are not limited to use in the biological sciences, and can find wide application in a variety of preparative and analytical contexts.

BRIEF DESCRIPTION OF THE FIGURES

FIG. 3A is a graph of a ubiquitin purification comparing different concentrations of imidazole in the wash and elution buffers. FIG. 3B is a graph of a pho protein purification comparing different concentrations of imidazole in the wash and elution buffers.

DESCRIPTION OF SPECIFIC EMBODIMENTS OF THE INVENTION

Figure 1:
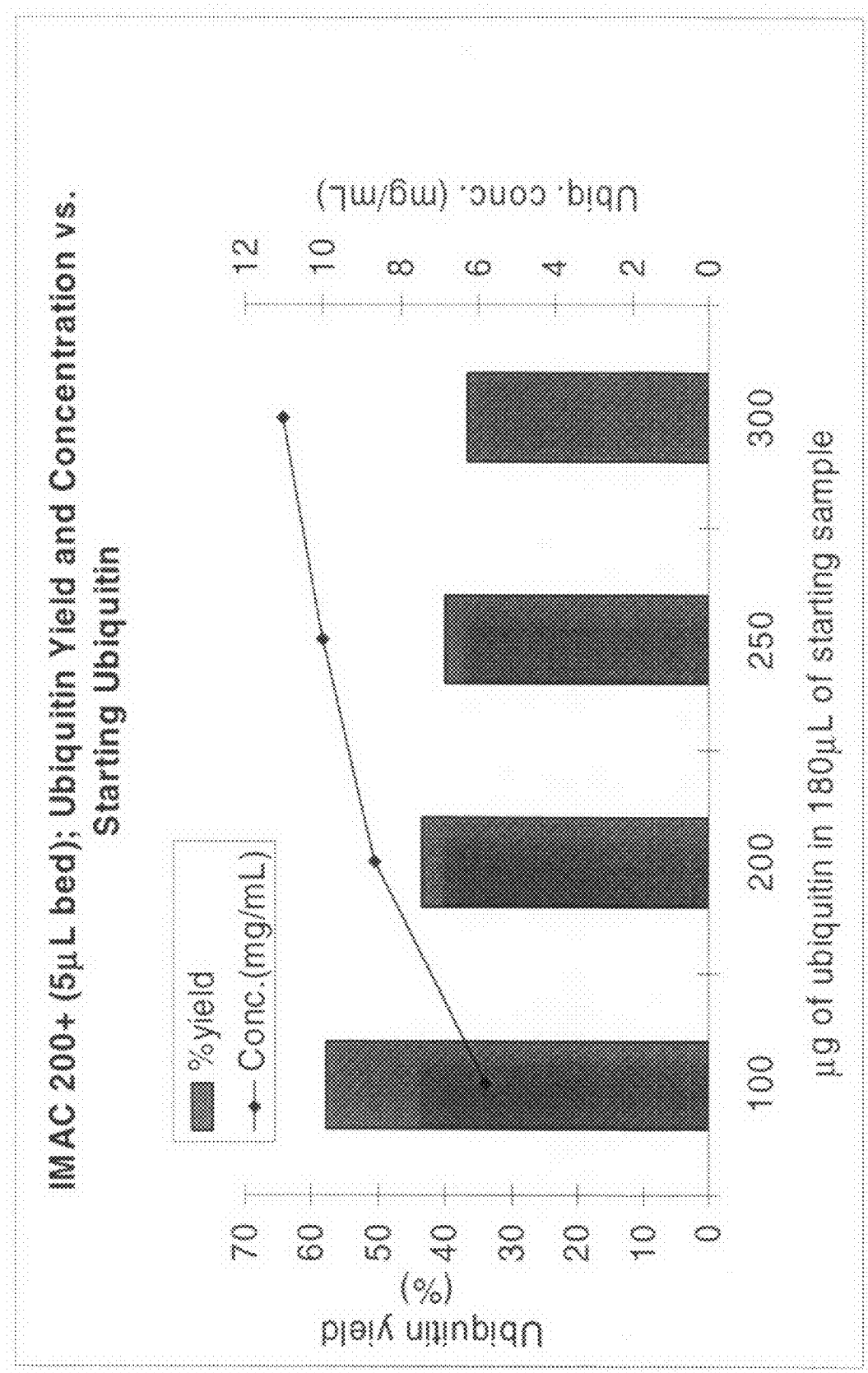
FIG. 1 is a graph comparing ubiquitin yield and concentration for four different starting amounts of ubiquitin.

This invention relates to methods and devices for extracting an analyte from a sample solution and then concentrating the analyte. The analytes can include biomolecules, particularly biological macromolecules such as proteins and polypeptides and complexes containing these molecules. The device and method of this invention are particularly useful in proteomics for sample preparation and analysis with analytical technologies employing biochips, mass spectrometry and other instrumentation. The extraction process generally results in the enrichment, concentration, and/or purification of an analyte or analytes of interest.

In U.S. patent application Ser. No. 10/620,155, incorporated by reference herein in its entirety, methods and devices for performing low dead column extractions are described. The instant specification, inter alia, expands upon the concepts described in that application.

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like.

All publications and patents mentioned in this specification are herein incorporated by reference into the specification to the same extent as if each individual publication or patent was specifically and individually indicated to be incorporated herein by reference.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

Definitions

Unless defined otherwise, all technical and scientific terms used herein have the same meaning as commonly understood by one of ordinary skill in the art to which the invention pertains. The following references provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, The Harper Collins Dictionary of Biology (1991). As used herein, the following terms have the meanings ascribed to them unless specified otherwise.

In describing and claiming the present invention, the following terminology will be used in accordance with the definitions set out below.

"Analyte" refers to a component of a sample which is desirably retained and detected. The term can refer to a single component or a set of components in the sample.

The term "biomolecule" as used herein refers to molecules derived from, or used with a biological system. The term includes biological macromolecules, such as proteins, peptides, carbohydrates, metabolites, polysaccharides, nucleic acids and small organic molecules.

"Complex" refers to analytes formed by the union of two or more biomolecules.

"Adsorb" refers to the detectable binding between binding functionalities of an adsorbent (e.g., a hydrogel material or agarose particles) and an analyte either before or after washing with an eluant (selectivity threshold modifier). The terms "adsorb" and "capture" are used interchangeable herein.

The term "bed volume" as used herein is defined as the volume of a bed of extraction medium in an extraction column. Depending on how densely the bed is packed, the volume of the extraction medium in the column bed is typically about one third to two thirds of the total bed volume; well packed beds have less space between the beads and hence generally have lower interstitial volumes.

The term "interstitial volume" of the bed refers to the volume of the bed of extraction medium that is accessible to solvent, e.g., aqueous sample solutions, wash solutions and desorption solvents. For example, in the case where the extraction medium is a chromatography bead (e.g., agarose or sepharose), the interstitial volume of the bed constitutes the solvent accessible volume between the beads, as well as any solvent accessible internal regions of the bead, e.g., solvent accessible pores. The interstitial volume of the bed represents the minimum volume of liquid required to saturate the column bed.

The term "dead volume" as used herein with respect to a column is defined as the interstitial volume of the extraction bed, tubes, membrane or frits, and passageways in a column.

Some preferred embodiments of the invention involve the use of low dead volume columns, as described in more detail in U.S. patent application Ser. No. 10/620,155.

The term "elution volume" as used herein is defined as the volume of desorption or elution liquid into which the analytes are desorbed and collected. The terms "desorption solvent," "elution liquid" and the like are used interchangeably herein.

The term "enrichment factor" as used herein is defined as the ratio of the sample volume divided by the elution volume, assuming that there is no contribution of liquid coming from the dead volume. To the extent that the dead volume either dilutes the analytes or prevents complete adsorption, the enrichment factor is reduced.

The terms "extraction column" and "extraction tip" as used herein are defined as a column device used in combination with a pump, the column device containing a bed of solid phase extraction material, i.e., extraction media.

The term "frit" as used herein is defined as porous material for holding the extraction medium in place in a column. An extraction medium chamber is typically defined by a top and bottom frit positioned in an extraction column. In preferred embodiments of the invention the frit is a thin, low pore volume filter, e.g., a membrane screen.

The term "lower column body" as used herein is defined as the column bed and bottom membrane screen of a column.

The term "membrane screen" as used herein is defined as a woven or non-woven fabric or screen for holding the column packing in place in the column bed, the membranes having a low dead volume. The membranes are of sufficient strength to withstand packing and use of the column bed and of sufficient porosity to allow passage of liquids through the column bed. The membrane is thin enough so that it can be sealed around the perimeter or circumference of the membrane screen so that the liquids flow through the screen.

The term "sample volume", as used herein is defined as the volume of the liquid of the original sample solution from which the analytes are separated or purified.

The term "upper column body", as used herein is defined as the chamber and top membrane screen of a column.

The term "pipette tip column size", as used herein is defined as the size of the pipette tip from which the pipette tip column was manufactured.

"Biological sample" refers to a sample derived from a virus, bacteria, cell, tissue, organ or organism including, without limitation, cell, tissue or organ lysates or homogenates, or body fluid samples, such as blood, urine or cerebrospinal fluid.

The term "sample solution" is defined herein as a solution containing an analyte. The terms "solution" and "solvent" are used interchangeably herein.

The term "biomolecule" as used herein refers to molecules derived from or used with a biological system. The term includes biological macromolecules, such as a proteins, peptides, carbohydrates, metabolites, polysaccharides, and nucleic acids.

The term "resin capacity" is defined as the amount of material that can be captured per unit volume of resin. In many cases, the capacity of the resin depends on the specific protein being captured. This is because proteins vary in size and affinity to the resin.

The "column capacity" is the amount of material that can be captured on a column under ideal conditions. During the first step of the 2-step process (purification conditions), the full column capacity is not likely to be used. Non-specifically bound material can be taken up by the resin and then removed by a wash solution leaving the column less than fully loaded.

Under the second step of the process (concentration), it is much more likely the resin will be highly loaded.

A "high concentration" of protein is defined as any concentration above 2, 5, 8, 10, 12, and 15 mg/mL. It can also be defined as any concentration sufficient for structural analysis work, such as x-ray crystallography.

Two-Step Purification Process

The two-step process of the invention is: 1) analyte purification and 2) analyte concentration. In some embodiments, the two steps are carried out using columns, such as extraction columns. In certain embodiments the columns are pipette tip columns. PhyTip columns (PhyNexus, Inc.) are particularly well-suited for use with the methods of the invention. In these embodiments the pipette tip columns can be attached to a pipettor or multi-channel pipettor.

In some embodiments, the first step involves using a first column to separate the analyte from any impurities or other material. The purification step is performed under conditions of high selectivity that produce pure analyte uniform in identity. Purity of the analyte is more important than concentration of the analyte. In this respect, the preferred column material for the first step is one that has high selectivity for the target analyte and one in which the selectivity for the non specific material can be controlled through capture conditions or wash conditions.

Although it is not required, the invention works best if the columns are loaded as much as possible in each step. In the first step, column loading is limited by the conditions chosen to minimize non-specific binding. Column washing used to remove non-specifically bound material will also lower the mass amount of pure analyte on the column. Washing and elution conditions are chosen so that only pure analyte is left on the column and is eluted. While as much analyte as possible is collected at this step, increasing the yield is not done at the expense of obtaining pure material.

During the first step of the process, the loading concentration is not as important as it is in the second step, although it can be high. In some embodiments the first column is loaded at a high concentration (at least 2 mg/ml). In some embodiments the analyte is a biomolecule, such as protein. In some embodiments, the protein can be eluted from the first column at a concentration greater than 1 mg/ml.

In some embodiments, the analyte is present in a relatively large volume of sample such that the analyte concentration is relatively dilute. In these embodiments, multiple sample aliquots may be passed through the column during the first step of the process. Alternatively, a dilute sample can be passed through the column more than one time, e.g., by being pumped back and forth through the bed. This can improve adsorption of analyte, which can be particularly helpful in cases where the analyte is of low abundance.

The purpose of the second step of the process is to produce high concentration analyte. Conditions are chosen in which the column used for second step is loaded completely. This means that substantially all or most of the available functional groups are loaded with the biological material of interest. Since it is important to load up the second column with as pure a material as possible, the amount delivered from the first column should ideally be more than the capacity of the second column.

The capacity of the second column may be much lower than the first to ensure that there is sufficient material to load the second column with pure material. The capacity of the second column may be between 5% lower and 99% lower depending on the mass amount required when the second elution is preformed. The analyte can be eluted from the second column with as small a volume of desorption solution as possible to produce a high concentration of very pure biological material.

The columns used in the first and second steps of the process can have the same chemistry or they may have different chemistries. Column chemistry refers to any chemistry used in solid-phase extraction or chromatography such as affinity, ion exchange, reverse phase, hydrophobic interaction, gel filtration and the like. Whether one chemistry or two different chemistries are used in practicing the invention, virtually any combination of chemistries can be used as long as purification is performed with the first chemistry and high loading is used with the second chemistry to produce very pure, and highly concentrated biological material. Column chemistry is discussed in greater detail below in the section entitled "Extraction media".

Extraction Columns

In accordance with the present invention there may be employed conventional chemistry, biological and analytical techniques within the skill of the art. Such techniques are explained fully in the literature. See, e.g. *Chromatography, 5th edition*, PART A: FUNDAMENTALS AND TECHNIQUES, editor: E. Heftmann, Elsevier Science Publishing Company, New York (1992); ADVANCED CHROMATOGRAPHIC AND ELECTROMIGRATION METHODS IN BIOSCIENCES, editor: Z. Deyl, Elsevier Science BV, Amsterdam, The Netherlands, (1998); CHROMATOGRAPHY TODAY, Colin F. Poole and Salwa K. Poole, and Elsevier Science Publishing Company, New York, (1991).

In some embodiments of the subject invention the packed bed of extraction medium is contained in a column, e.g., a low dead volume column. Non-limiting examples of suitable columns, particularly low dead volume columns, are presented herein. It is to be understood that the subject invention is not to be construed as limited to the use of extraction beds in low dead volume columns, or in columns in general. For example, the invention is equally applicable to use with a packed bed of extraction medium as a component of a multi-well plate.

Column Body

The column body is a tube having two open ends connected by an open channel. The tube can be in any shape, including but not limited to cylindrical or frustoconical, and of any dimensions consistent with the function of the column as described herein. In some preferred embodiments of the invention the column body takes the form of a pipette tip, a syringe, a luer adapter, a well on a multi-well plate (such as a filter plate) or similar tubular bodies. In embodiments where the column body is a pipette tip, the end of the tip wherein the bed of extraction medium is placed can take any of a number of geometries, e.g., it can be tapered or cylindrical. In some case a cylindrical channel of relatively constant radius can be preferable to a tapered tip, for a variety of reason, e.g., solution flows through the bed at a uniform rate, rather than varying as a function of a variable channel diameter.

In some embodiments, one of the open ends of the column, sometimes referred to herein as the open upper end of the column, is adapted for attachment to a pump. In some embodiments of the invention the upper open end is operatively attached to a pump, whereby the pump can be used for aspirating a fluid into the extraction column through the other open end of the column, and optionally for discharging fluid out through the open lower end of the column. Thus, it is a feature certain embodiments of the present invention that fluid enters and exits the extraction column through the same open end of the column. This is in contradistinction with the operation of some extraction columns, where fluid enters the column through one open end and exits through the other end after traveling through an extraction medium, i.e., similar to conventional column chromatography. The fluid can be a liquid, such as a sample solution, wash solution or desorption solvent. The fluid can also be a gas, e.g., air used to blow liquid out of the extraction column.

In other embodiments of the present invention, fluid enters the column through one end and exits through the other. In some embodiments, the invention provides extraction methods that involve a hybrid approach; that is, one or more fluids enter the column through one end and exit through the other, and one more fluids enter and exit the column through the same open end of the column, e.g., the lower end. Thus, for example, in some methods the sample solution and/or wash solution are introduced through the top of the column and exit through the bottom end, while the desorption solution enters and exits through the bottom opening of the column. Aspiration and discharge of solution through the same end of the column can be particularly advantageous in procedures designed to cycle the fluids back and forth. In cases where the sample enters in one end of the column and exits the other end, the sample and other fluids may be passed through the column multiple times by directing the effluent of the column to the inlet of a pump and directing the effluent of the pump to the inlet of the column. A peristaltic, diaphragm, piston or other type of pump could be used in this manner.

The column body can be can be composed of any material that is sufficiently non-porous that it can retain fluid and that is compatible with the solutions, media, pumps and analytes used. A material should be employed that does not substantially react with substances it will contact during use of the extraction column, e.g., the sample solutions, the analyte of interest, the extraction medium and desorption solvent. A wide range of suitable materials are available and known to one of skill in the art, and the choice is one of design. Various plastics make ideal column body materials, but other materials such as glass, ceramics or metals could be used in some embodiments of the invention. Some examples of preferred materials include polysulfone, polypropylene, polyethylene, polyethyleneterephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials.

Frits

In some embodiments of the invention one or more frits is used to contain the bed of extraction medium in, for example, a column. Frits can take a variety of forms, and can be constructed from a variety of materials, e.g., glass, ceramic, metal, fiber. Some embodiments of the invention employ frits having a low pore volume, which contribute to reducing dead volume. The frits of the invention are porous, since it is necessary for fluid to be able to pass through the frit. The frit should have sufficient structural strength so that frit integrity can contain the extraction medium in the column. It is desirable that the frit has little or no affinity for chemicals with which it will come into contact during the extraction process, particularly the analyte of interest. In many embodiments of the invention the analyte of interest is a biomolecule, particularly a biological macromolecule. Thus in many embodiments of the invention it desirable to use a frit that has a minimal tendency to bind or otherwise interact with biological macromolecules, particularly proteins, peptides and nucleic acids.

Frits of various pores sizes and pore densities may be used provided the free flow of liquid is possible and the beads are held in place within the extraction medium bed.

Certain embodiments of the invention employ a membrane screen as the frit. The membrane screen should be strong enough to not only contain the medium in the column bed, but also to avoid becoming detached or inadvertently punctured during the actual packing of the medium into the column bed. Membranes can be fragile, and in some embodiments must be contained in a framework to maintain their integrity during use. However, it is desirable to use a membrane of sufficient strength such that it can be used without reliance on such a framework. The membrane screen should also be flexible so that it can conform to the column bed. This flexibility is advantageous in the packing process as it allows the membrane screen to conform to the bed of medium, resulting in a reduction in dead volume. Frits are described in greater detail in published U.S. Patent application 20040072375 which is incorporated in its entirety herein.

Extraction Media

The extraction medium used in the column is preferably a form of water-insoluble particle (e.g., a porous or non-porous bead) that has an affinity for an analyte of interest. Extraction media may also be referred to herein as column media, resin, particles or beads. Typically, the analyte of interest is a protein, peptide or nucleic acid. The extraction processes can be affinity, reverse phase, normal phase, ion exchange, hydrophobic interaction chromatography, or hydrophilic interaction chromatography agents.

Methods of the invention involve a two-step purification process wherein each step is typically performed using one or more extraction columns. Columns used in the first step have a larger capacity than those used in the second step. The extraction medium bed volume in the column used for the first step of the process is in the range of 0.1 µL to 25 mL, typically in the range of 0.1-1000 µL, preferably in the range of 0.1-200 µL, e.g., in a range having a lower limit of 0.1, 0.5, 1, 1.5, 2, 2.5, 3, 5 or 10 µL; and an upper limit of 5, 10, 15, 20, 30, 40 50, 60, 70, 80, 90, 100, 150, 200, 300, 400, 500 µL, 1 mL, 5 mL, 10 mL or 25 mL.

The extraction medium bed volume for the column used in the second step of the process is smaller than that used in the first step. Usually, the bed volume is 0.1% to 95% of the bed volume used in the first step. The bed volume of columns used in the step two can be 25%, 30%, 35%, 40%, 45%, 50%, 55%, 6%, 65%, 70% or 75% of the bed volume of the columns used in the first step of the process. In terms of ranges, the bed volume of columns used in the step two can be 1-99%, 5-90%, 10-50% or 15-40% of the bed volume of the columns used in the first step of the process.

The low bed volumes employed in certain embodiments allow for the use of different amounts of extraction media, e.g., soft, gel-type beads. For example, some embodiments of the invention employ a bed of extraction medium having a dry weight of less than 20 grams (e.g., in the range of 0.001-20 g, 0.005-5 g, 0.01-1 g or 0.02-1 g), less than 100 mg (e.g., in the range of 0.1-100 mg, 0.5-100 mg, 1-100 mg 2-100 mg, or 10-100 mg), less than 10 mg (e.g., in the range of 0.1-10 mg, 0.5-10 mg, 1-10 mg or 2-10 mg), less than 2 mg (e.g., in the range of 0.1-2 mg, 0.5-2 mg or 1-2 mg), or less than 1 mg (e.g., in the range of 0.1-1 mg or 0.5-1 mg).

As described above for bed volume, the capacity of the extraction medium in those columns used in step two of the process will be lower than the capacity of extraction medium used in step one columns. In some embodiments, the capacity of extraction medium used in step two columns can be between 0.1% and 90% of the capacity used for columns utilized in the first step of the process. In certain embodiments, the capacity of extraction medium in step two columns is 1%, 5%, 10%, 15%, 20%, 25%, 30%, 35%, 40%, 45%, 50%

55% 60% 65%, 70% or 75% of the capacity used in columns used in the first step of the process. Expressed in terms of ranges, the capacity of columns used in the step two can be 1-95%, 5-90%, 10-50% or 15-40% of the capacity of the columns used in the first step of the process.

Many of the extraction media suitable for use in the invention are selected from a variety of classes of chromatography media. It has been found that many of these chromatography media and the associated chemistries are suited for use as solid phase extraction media in the devices and methods of this invention. Affinity and ion exchange chemistries are described in greater detail below.

Affinity chemistry includes IMAC purification chemistry of His tagged recombinant proteins, Protein A, Protein G, and Protein L chemistry purification of antibodies, and others listed in Table I. In step one, purification can be performed with reagents in the capture and wash that compete for the affinity sites. An example of this is the addition of imidazole to the capture and wash solutions during purification of an his-tagged protein on a Ni-NTA extraction column. The concentration of imidazole is kept much lower than what is needed for the elution step, typically 5-20 mM in the capture and wash solution vs. 300 mM imidazole in the elution solution. The concentration in the capture and wash depends on how selective the protein is for the IMAC resin. Highly selectively held proteins can be washed with fairly high imidazole without danger of losing too much of the protein. Non specific bound materials can be removed while the target protein remains tightly on the column. Proteins that are held less tightly are washed with lower concentrations of imidazole so that loss of the protein is less. Once the protein is purified on the IMAC column, the protein may be recovered using low pH, a competing chelator such as EDTA, or high concentrations of imidazole (e.g., 500 mM). Choice of the eluting solution depends on what the second column chemistry used. In the case of using the same chemistry again, low pH elution might be most desirable because the pH may be simply raised up to 7 or 7.5 for recapture on the second step. If the second column chemistry is ion exchange, imidazole might be preferable depending on the pKa of the protein and type of ion exchanger used.

Ion exchange extraction can be used during the first and/or second step of the process. Ion exchange extraction relies on charge-charge interactions between the proteins in the sample and the charges immobilized on the resin. Ion exchange extraction can be subdivided into cation exchange extraction, in which positively charged ions bind to a negatively charged resin; and anion exchange extraction, in which the binding ions are negative, and the immobilized functional group is positive. Once the solutes are bound, the column may be washed to remove non-specifically bound material. This is accomplished using a gradient of a second buffer which steadily increases the ionic strength of the eluent solution. Alternatively, the pH of the elution buffer can be modified to give the protein or the medium a charge at which they will not interact and the analyte of interest elutes from the resin.

If the analyte is negatively charged at the desired pH, an anion exchanger can be used. Conversely, if the analyte is positively charged, a cation exchanger can be used. For a weak acid cation exchanger, elution can be performed with another competing cation or by lowering the buffer pH. For a strong acid cation exchanger elution is usually performed with another competing driving cation. If the protein is an anion, an anion exchanger can be used for capture. For a weak base cation exchanger, elution can be performed with another competing anion or by raising the pH. For a strong base anion exchanger elution is usually performed with another competing driving anion.

Commonly used anion exchange resins are Q-resin, a Quaternary amine; and DEAE resin, diethylaminoethane anion exchange extraction. Typically, anion exchange extraction is performed using buffers at pH's between 7 and 10 and running a gradient from a solution containing just this buffer to a solution containing this buffer with 1M NaCl. The salt in the solution competes for binding to the immobilized matrix and releases the protein from its bound state at a given concentration. Proteins can be extracted because the amount of salt needed to compete varies with the external charge of the protein. Uses of anion exchange extraction include initial clean up of a crude slurry, separation of proteins from each other, concentrating a protein, and the removal of negatively charged endotoxin from protein preparations.

Cation exchange extraction is also used for protein purification. The surface charge of the solutes (proteins, nucleic acids, endotoxin) which bind will be net positive, thus to get binding of a specific protein one should be below the pI of that protein. Commonly used cation exchange resins are S-resin, sulfate derivatives; and CM resins, carboxylate derived ions.

Cation exchange extraction is less commonly used than anion exchange extraction, largely due to the fact that often proteins do not adsorb to this resin at physiological pH and it is not advisable to titrate a protein through its isoelectric point in order to get it to get adsorption. Nonetheless, it is as powerful as anion exchange extraction for initial separations with equivalently high capacity. Typically, cation exchange extraction is performed using buffers at pH between 4 and 7 and running a gradient from a solution containing just this buffer to a solution containing this buffer with 1M NaCl. Uses of cation exchange extraction include initial clean up of a crude slurry, separation of proteins from each other, concentrating a protein, and as a common first purification step for proteins expressed under acidic conditions such as in *P. pastoris*.

Examples of suitable extraction media include resin beads used for extraction and/or chromatography. Preferred resins include gel resins, pellicular resins, and macroporous resins. The term "macroporous resin" refers to highly crosslinked resins having high surface area due to a physical porous structure that formed during the polymerization process. Generally an inert material (such as a solid or a liquid that does not solvate the polymer that is formed) is polymerized with the bead and then later washed out, leaving a porous structure. Crosslinking of macroporous materials range from 5% to 90% with perhaps a 25 to 55% crosslinking the most common materials. Macroporous resins behave similar to pellicular resins except that in effect much more surface area is available for interaction of analyte with resin functional groups.

The term "pellicular resins" refers to materials in which the functional groups are on the surface of the bead or in a thin layer on the surface of the bead. The interior of the bead is solid, usually highly crosslinked, and usually inaccessible to the solvent and analytes. Pellicular resins generally have lower capacities than gel and macroporous resins.

Gel resins can be non-porous or micro-porous beads. The term "gel resin" refers to a resin comprising low-crosslinked bead materials that can swell in a solvent, e.g., upon hydration. Crosslinking refers to the physical linking of the polymer chains that form the beads. The physical linking is normally accomplished through a crosslinking monomer that contains bi-polymerizing functionality so that during the polymerization process, the molecule can be incorporated into two different polymer chains. The degree of crosslinking for a particular material can range from 0.1 to 30%, with 0.5 to 10% normally used. 1 to 5% crosslinking is most common. A lower degree of crosslinking renders the bead more permeable to solvent, thus making the functional sites within the bead more accessible to analyte. However, a low crosslinked bead can be deformed easily, and should only be used if the flow of eluent through the bed is slow enough or gentle enough to prevent closing the interstitial spaces between the beads, which could then lead to catastrophic collapse of the bed. Higher crosslinked materials swell less and may prevent access of the analytes and desorption materials to the interior functional groups within the bead. Generally, it is desirable to use as low a level of crosslinking as possible, so long is it is sufficient to withstand collapse of the bed. This means that in conventional gel-packed columns, slow flow rates may have to be used. In the present invention the back pressure is very low, and high liquid flow rates can be used without collapsing the bed. Surprisingly, using these high solvent velocities does not appear to reduce the capacity or usefulness of the bead materials. Non-limiting examples of gel resins include agarose, sepharose, polystyrene, polyacrylate, cellulose, silica, diamond, glycidyl methacrylate (GMA) copolymerized with divinylbenzene (DVB), polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection and others. In some embodiments, the medium is comprised of a mixture of two or more gel resins.

Gel resins can swell 10 to 99% by volume when contacted with the solvent, preferably water. The agarose and sepharose affinity resins usually swell more than 50% and can swell up to 99%, depending on crosslinking when contacted with water. Low crosslinked resins swell more. In the column format of the invention, extremely swellable or deformable beads can be used.

Examples of resins beads include polystyrene/divinylbenzene copolymers, poly methylmethacrylate, protein G beads (e.g., for IgG protein purification), MEP Hypercel™ beads (e.g., for IgG protein purification), affinity phase beads (e.g., for protein purification), ion exchange phase beads (e.g., for protein purification), hydrophobic interaction beads (e.g., for protein purification), reverse phase beads (e.g., for nucleic acid or protein purification), and beads having an affinity for molecules analyzed by label-free detection. Silica beads are also suitable.

Soft gel resin beads, such as agarose and sepharose based beads, are found to work surprisingly well in columns and methods of this invention. In conventional chromatography fast flow rates can result in bead compression, which results in increased back pressure and adversely impacts the ability to use these gels with faster flow rates. In the present invention relatively small bed volumes are used, and it appears that this allows for the use of high flow rates with a minimal amount of bead compression and the problem attendant with such compression.

The bead size that may be used depends somewhat on the bed volume and the cross sectional area of the column. A lower bed volume column will tolerate a smaller bead size without generating the high backpressures that could burst a thin membrane frit. For example a bed volume of 0.1 to 1 μL bed, can tolerate 5 to 10 μm particles. Larger beds (up to about 50 μL) normally have beads sizes of 30-150 μm or higher. The upper range of particle size is dependent on the diameter of the column bed. The bead diameter size should not be more than 50% of the bed diameter, and preferably less than 10% of the bed diameter.

The extraction chemistry employed in the present invention can take any of a wide variety of forms. For example, the extraction medium can be selected from, or based on, any of the extraction chemistries used in solid-phase extraction and/or chromatography, e.g., reverse-phase, normal phase, hydrophobic interaction, hydrophilic interaction, ion-exchange, thiophilic separation, hydrophobic charge induction or affinity binding. Because the invention is particularly suited to the purification and/or concentration of biomolecules, extraction surfaces capable of adsorbing such molecules are particularly relevant. See, e.g., SEPARATION AND SCIENCE TECHNOLOGY Vol. 2.:HANDBOOK OF BIOSEPARATIONS, edited by Satinder Ahuja, Academic Press (2000).

Affinity extractions use a technique in which a biospecific adsorbent is prepared by coupling a specific ligand (such as an enzyme, antigen, or hormone) for the analyte, (e.g., macromolecule) of interest to a solid support. This immobilized ligand will interact selectively with molecules that can bind to it. Molecules that will not bind elute unretained. The interaction is selective and reversible. The references listed below show examples of the types of affinity groups that can be employed in the practice of this invention are hereby incorporated by reference herein in their entireties. Antibody Purification Handbook, *Amersham Biosciences*, Edition AB, 18-1037-46 (2002); Protein Purification Handbook, *Amersham Biosciences*, Edition AC, 18-1132-29 (2001); Affinity Chromatography Principles and Methods, *Amersham Pharmacia Biotech*, Edition AC, 18-1022-29 (2001); The Recombinant Protein Handbook, *Amersham Pharmacia Biotech*, Edition AB, 18-1142-75 (2002); and *Protein Purification: Principles, High Resolution Methods, and Applications*, Jan-Christen Janson (Editor), Lars G. Ryden (Editor), Wiley, John & Sons, Incorporated (1989).

Examples of suitable affinity binding agents are summarized in Table I, wherein the affinity agents are from one or more of the following interaction categories:
  1. Chelating metal—ligand interaction
  2. Protein—Protein interaction
  3. Organic molecule or moiety—Protein interaction
  4. Sugar—Protein interaction
  5. Nucleic acid—Protein interaction

TABLE I

| Examples of Affinity molecule or moiety fixed at surface | Captured biomolecule | Interaction Category |
|---|---|---|
| Ni-NTA | His-tagged protein | 1 |
| Ni-NTA | His-tagged protein within a multi-protein complex | 1, 2 |
| Fe-IDA | Phosphopeptides, phosphoproteins | 1 |
| Fe-IDA | Phosphopeptides or phosphoproteins within a multi-protein complex | 1, 2 |
| Cu-IDA | Phosphopeptides, phosphoproteins | 1 |
| Co-IDA | Phosphopeptides, phosphoproteins | 1 |
| Zn-IDA | Phosphopeptides, phosphoproteins | 1 |
| Mn-IDA | Phosphopeptides, phosphoproteins | 1 |
| Al-IDA | Phosphopeptides, | 1 |

TABLE I-continued

| Examples of Affinity molecule or moiety fixed at surface | Captured biomolecule | Interaction Category |
|---|---|---|
| Ga-IDA | phosphoproteins Phosphopeptides, phosphoproteins | 1 |
| Antibody or other Proteins | Protein antigen | 2 |
| Antibody or other Proteins | Small molecule-tagged protein | 3 |
| Antibody or other Proteins | Small molecule-tagged protein within a multi-protein complex | 2, 3 |
| Antibody or other Proteins | Protein antigen within a multi-protein complex | 2 |
| Antibody or other Proteins | Epitope-tagged protein | 2 |
| Antibody or other Proteins | Epitope-tagged protein within a multi-protein complex | 2 |
| Protein A, Protein G or Protein L | Antibody | 2 |
| Protein A, Protein G or Protein L | Antibody | 2 |
| ATP or ATP analogs; 5'-AMP | Kinases, phosphatases (proteins that requires ATP for proper function) | 3 |
| ATP or ATP analogs; 5'-AMP | Kinase, phosphatases within multi-protein complexes | 2, 3 |
| Cibacron 3G | Albumin | 3 |
| Heparin | DNA-binding protein | 4 |
| Heparin | DNA-binding proteins within a multi-protein complex | 2, 4 |
| Lectin | Glycopeptide or glycoprotein | 4 |
| Lectin | Glycopeptide or glycoprotein within a multi-protein complex | 2, 4 |
| ssDNA or dsDNA | DNA-binding protein | 5 |
| ssDNA or dsDNA | DNA-binding protein within a multi-protein complex | 2, 5 |
| Streptavidin/Avidin | Biotinylated peptides (ICAT) | 3 |
| Streptavidin/Avidin | Biotinylated engineered tag fused to a protein (see avidity.com) | 3 |
| Streptavidin/Avidin | Biotinylated protein | 3 |
| Streptavidin/Avidin | Biotinylated protein within a multi-protein complex | 2, 3 |

In one aspect of the invention an extraction medium is used that contains a surface functionality that has an affinity for a protein fusion tag used for the purification of recombinant proteins. A wide variety of fusion tags and corresponding affinity groups are available and can be used in the practice of the invention.

U.S. patent application Ser. No. 10/620,155 describes in detail the use of specific affinity binding reagents in solid-phase extraction. Examples of specific affinity binding agents include proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA); glutathione surfaces-nucleotides, oligonucleotides, polynucleotides and their analogs (e.g., ATP); lectin surface-heparin surface-avidin or streptavidin surface, a peptide or peptide analog (e.g., that binds to a protease or other enzyme that acts upon polypeptides).

In some embodiments of the invention, the affinity binding reagent is one that recognizes one or more of the many affinity groups used as affinity tags in recombinant fusion proteins. Examples of such tags include poly-histidine tags (e.g., the 6X-His tag), which can be extracted using a chelated metal such as Ni-NTA-peptide sequences (such as the FLAG epitope) that are recognized by an immobilized antibody; biotin, which can be extracted using immobilized avidin or streptavidin; "calmodulin binding peptide" (or, CBP), recognized by calmodulin charged with calcium-glutathione S-transferase protein (GST), recognized by immobilized glutathione; maltose binding protein (MBP), recognized by amylose; the cellulose-binding domain tag, recognized by immobilized cellulose; a peptide with specific affinity for S-protein (derived from ribonuclease A); and the peptide sequence tag CCxxCC (where xx is any amino acid, such as RE), which binds to the affinity binding agent bis-arsenical fluorescein (FlAsH dye).

Antibodies can be extracted using, for example, proteins such as protein A, protein G, protein L, hybrids of these, or by other antibodies (e.g., an anti-IgE for purifying IgE).

Chelated metals are not only useful for purifying poly-his tagged proteins, but also other non-tagged proteins that have an intrinsic affinity for the chelated metal, e.g., phosphopeptides and phosphoproteins.

Antibodies can also be useful for purifying non-tagged proteins to which they have an affinity, e.g., by using antibodies with affinity for a specific phosphorylation site or phosphorylated amino acids.

In other embodiments of the invention extraction surfaces are employed that are generally less specific than the affinity binding agents discussed above. These extraction chemistries are still often quite useful. Examples include ion exchange, reversed phase, normal phase, hydrophobic interaction and hydrophilic interaction extraction or chromatography surfaces. In general, these extraction chemistries, methods of their use, appropriate solvents, etc. are well known in the art, and in particular are described in more detail in U.S. patent application Ser. Nos. 10/434,713 and 10/620,155, and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 3 94 (1991); and ORGANIC SYNTHESIS ON SOLID PHASE, F. Dorwald Wiley VCH Verlag Gmbh, Weinheim 2002.

Extraction Column Assembly

The extraction columns of the invention can be constructed by a variety of methods using the teaching supplied herein. In some embodiments the extraction column can be constructed by the engagement (i.e., attachment) of upper and lower tubular members (i.e., column bodies) that combine to form the extraction column. In certain embodiments of the column manufacturing process, the inner column body is stably affixed to the outer column body by frictional engagement with the surface of the open channel.

In some embodiments of this general method of column manufacture, the entire inner column body is disposed within the first open channel. In these embodiments the first open upper end is normally adapted for operable attachment to a pump, e.g., the outer column body is a pipette tip and the pump is a pipettor. In some embodiments, the outer diameter of the inner column body tapers towards its open lower end, and the open channel of the outer column body is tapered in the region where the inner column body frictionally engages the open channel, the tapers of the inner column body and open channel being complementary to one another. This complementarity of taper permits the two bodies to fit snuggly together and form a sealing attachment, such that the resulting column comprises a single open channel containing the bed of extraction medium bounded by the two frits. Examples of suitable column configurations are given in published U.S. Patent Applications 20040072375 and 20050255604 each of which is incorporated herein by reference.

Solvents

Extractions of the invention typically involve the loading of analyte in a sample solution, an optional wash with a rinse solution, and elution of the analyte into a desorption solution. The nature of these solutions will now be described in greater detail.

With regard to the sample solution, it typically consists of the analyte dissolved in a solvent in which the analyte is soluble, and in which the analyte will bind to the extraction surface. Preferably, the binding is strong, resulting in the binding of a substantial portion of the analyte, and optimally substantially all of the analyte will be bound under the loading protocol used in the procedure. The solvent should also be gentle, so that the native structure and function of the analyte is retained upon desorption from the extraction surface. Typically, in the case where the analyte is a biomolecule, the solvent is an aqueous solution, typically containing a buffer, salt, and/or surfactants to solubilize and stabilize the biomolecule. Examples of sample solutions include cells lysates, hybridoma growth medium, cell-free translation or transcription reaction mixtures, extracts from tissues, organs, or biological samples, and extracts derived from biological fluids.

It is important that the sample solvent not only solubilize the analyte, but also that it is compatible with binding to the extraction phase. For example, where the extraction phase is based on ion exchange, the ionic strength of the sample solution should be buffered to an appropriate pH such that the charge of the analyte is opposite that of the immobilized ion, and the ionic strength should be relatively low to promote the ionic interaction. In the case of a normal phase extraction, the sample loading solvent should be non-polar, e.g., hexane, toluene, or the like. Depending upon the nature of the sample and extraction process, other constituents might be beneficial, e.g., reducing agents, detergents, stabilizers, denaturants, chelators, metals, etc.

A wash solution, if used, should be selected such that it will remove non-desired contaminants with minimal loss or damage to the bound analyte. The properties of the wash solution are typically intermediate between that of the sample and desorption solutions.

Desorption solvent can be introduced as either a stream or a plug of solvent. If a plug of solvent is used, a buffer plug of solvent can follow the desorption plug so that when the sample is deposited on the target, a buffer is also deposited to give the deposited sample a proper pH. An example of this is desorption from a protein G surface of IgG antibody which has been extracted from a hybridoma solution. In this example, 10 mM phosphoric acid plug at pH 2.5 is used to desorb the IgG from the tube. A 100 mM phosphate buffer plug at pH 7.5 follows the desorption solvent plug to bring the deposited solution to neutral pH. The deposited material can then be analyzed, e.g., by deposition on an SPR chip.

The desorption solvent should be just strong enough to quantitatively desorb the analyte while leaving strongly bound interfering materials behind. The solvents are chosen to be compatible with the analyte and the ultimate detection method.

In the case where the extraction involves binding of analyte to a specific cognate ligand molecule, e.g., an immobilized metal, the desorption solvent can contain a molecule that will interfere with such binding, e.g., imidazole or a metal chelator in the case of the immobilized metal.

Examples of suitable phases for solid phase extraction and desorption solvents are shown in Table A.

TABLE A

| | Ion Exchange Extraction | Affinity Phase Extraction |
|---|---|---|
| Typical solvent polarity range | High | High |
| Typical sample loading solvent | $H_2O$, buffers | $H_2O$, buffers |
| Typical desorption solvent | Buffers, salt solutions | $H_2O$, buffers, pH, competing reagents, heat, solvent polarity |
| Sample elution selectivity | Sample components most weakly ionized first | Non-binding, low-binding, high-binding |
| Solvent change required to desorb | Increase ionic strength or increase retained compounds pH or decrease pH | Change pH, add competing reagent, change solvent polarity, adjust heat |

Methods for Using the Extraction Columns

Methods of the invention involve two steps; purification followed by concentration. The first step removes impurities from a sample solution. The sample solution can be any solution containing an analyte of interest. The invention is particularly useful for extraction and purification of biological molecules, hence the sample solution is often of biological origin, e.g., a cell lysate. In one embodiment of the invention the sample solution is a hybridoma cell culture supernatant. Certain embodiments of the invention are particularly suited to the processing of biological samples, where the analyte of interest is a biomolecule. Of particular relevance are biological macromolecules such as polypeptides, proteins, or complexes containing one or more of this moiety. In certain embodiments, the polypeptides, proteins and complexes recovered from the process remain active.

In certain embodiments columns such as extraction columns are used for both steps of the invention. In certain embodiments, the columns are used with automated liquid handling instrumentation such as the MEA™ personal purification system (PhyNexus, Inc., San Jose, Calif.). In certain embodiments, the columns are pipette-tip columns. This process can be applied to a number of different column configurations and column chemistries. PhyTip® pipette-tip columns (PhyNexus, Inc., San Jose, Calif.) are especially well-suited for the use with the instant invention. One advantage afforded by PhyTip columns is that a very low elution volume can be used resulting in high concentrations of the biological material. High concentrations of recovered material are useful in the first step and are particularly useful in the second step of the process of the invention.

Generally the invention involves introducing a sample solution containing an analyte of interest into an extraction column containing a packed bed of extraction medium. (Extraction columns are described above in the Extraction columns and Column body sections.) The sample can be conveniently introduced into the packed bed of medium by pumping the solution through the column. Note that the volume of sample solution can be much larger than the bed volume. Material can be pumped through the column in one direction as long as enough as there is sufficient feed or the material may be re-circulated. The sample solution can optionally be passed through the column more than one time, e.g., by being pumped back and forth through the bed. This can improve adsorption of analyte, which can be particularly helpful in cases where the analyte is of low abundance and hence maximum sample recovery is desired.

For the first step, conditions are chosen for the capture and/or wash steps that will produce pure material. While as much material as possible will be collected at this step, increasing the yield is not done at the expense of obtaining impure material. After the purification step, the material may be pH adjusted, desalted, or treated in preparation for the second step of the process. This is especially important in cases where the second column chemistry is the same as the first column chemistry but may also be important where the two column chemistries are different. Columns used in the second step are lower in total column capacity than those used in the first step. The second step produces high concentrations of the biological molecule (at least 2 mg/ml). In some embodiments of the invention, columns used in the first and second steps will have the same column chemistry. That is, the functional group of the column resin is the same in both steps. In these embodiments, the sample is adjusted (e.g., pH) between the first and second steps so that the sample can be taken up again by the same chemistry. In other embodiments of the invention, two different column chemistries are used. When two chemistries are used in practicing the invention, virtually any combination of chemistries can be used. The function of columns used in the first step remains the same i.e. to purify the biological material. Purity of the material is more important than the concentration. In that respect, the preferred column material for the first column is one that will have high selectivity for the target material and one in which the selectivity for the non specific material can be controlled through capture conditions or wash conditions. The second column is simply one in which the purified material can be highly loaded and eluted in a concentrated manner.

As described above, the extraction medium in the first column may be different or the same as that used in the second column. For example for an IMAC purification of a recombinant protein, conditions are chosen so that very pure material is captured. This can be accomplished by using a relatively high concentration of imidazole (5-25 mM) in the capture and in the wash. The wash is performed so that all non-specifically bound material is removed from the column. Then the column is eluted to produce the pure protein although the protein might be fairly dilute. Elution might be accomplished by removing the captured and washed protein from the column with low pH buffer (e.g. citrate buffer, pH 4). Following elution, the protein is neutralized with carbonate to pH 7.4.

Next, a second column is loaded. The chemistry of the second column might be IMAC or ion exchange for example. If an IMAC column is used, it is no longer necessary to use imidazole in the capture and wash steps since the protein is already pure. In any case, the column is preferably lower capacity than the first so that the column can be completely loaded. The capacity may be 1% lower, 5% lower, 10% lower, 15% lower, 20% lower, 25% lower, 30% lower, 35% lower, 40% lower, 45% lower, 50% lower, 60% lower, 65% lower, 70% lower, 75% lower, 80% lower, 85% lower, 90% lower, 95% lower, down to 99% lower depending on the mass amount required when the second elution is performed. In some embodiments, the concentration of the protein eluted from the second column can be up to 10 mg/ml or more.

In some embodiments the second chemistry is chosen so that high concentration elution can be performed without precipitating or agglomerating the target material. In these embodiments, ion exchange might be preferable to IMAC because the elution buffer can be chosen specifically to prevent precipitation or agglomeration and recover the protein in a highly concentrated pure state.

In some embodiments, PhyTip Protein A columns are used for both steps of the process. For example, the first step may be IgG purification using Protein A affinity resin. Protein captured on the column may be washed with an intermediate pH buffer to remove weakly bound material. Or the column may simply be washed extensively with a high pH buffer or a saline buffer to remove non-specifically bound material and weakly bound material. The elution is performed under low pH conditions after which the pH is neutralized with base or a buffer. The neutralization step not only stabilizes the sample, it prepares the sample for a second capture with a second column of lower capacity. The second column is loaded up as much as possible so that upon elution, high concentrations of material are produced.

After the sample solution has been introduced into the bed and analyte allowed to adsorb, the sample solution is substantially evacuated from the bed, leaving the bound analyte. It is not necessary that all sample solution be evacuated from the bed, but diligence in removing the solution can improve the purity of the final product. An optional wash step between the adsorption and desorption steps can also improve the purity of the final product. Typically water, saline, or a buffer is used for the wash solution. The wash solution is preferably one that will, with a minimal desorption of the analyte of interest, remove excess matrix materials, lightly adsorbed or non-specifically adsorbed materials so that they do not come off in the elution cycle as contaminants. The wash cycle can include solvent or solvents having a specific pH, or containing components that promote removal of materials that interact lightly with the extraction phase. In some cases, several wash solvents might be used in succession to remove specific material, e.g., PBS followed by water or saline. These cycles can be repeated as many times as necessary. In other cases, where light contamination can be tolerated, a wash cycle can be omitted.

The volume of desorption solvent used can be very small, approximating the interstitial volume of the bed of extraction medium. In preferred embodiments of the invention the amount of desorption solvent used is less than 10-fold greater than the interstitial volume of the bed of extraction medium, more preferably less than 5-fold greater than the interstitial volume of the bed of extraction medium, still more preferably less than 3-fold greater than the interstitial volume of the bed of extraction medium, still more preferably less than 2-fold greater than the interstitial volume of the bed of extraction medium, and most preferably is equal to or less than the interstitial volume of the bed of extraction medium. The use of small volumes of desorption solution enables one to achieve high enrichment factors in the described methods. The term "enrichment factor" as used herein is defined as the ratio of the sample volume divided by the elution volume, assuming that there is no contribution of liquid coming from the dead volume. To the extent that the dead volume either dilutes the analytes or prevents complete adsorption, the enrichment factor is reduced. For example, if 1000 μL of sample solution is loaded onto the column and the bound analyte eluted in 10 μL of desorption solution, the calculated enrichment factor is 100. Note that the calculated enrichment factor is the maximum enrichment that can be achieved with complete capture and release of analyte. Actual achieved enrichments will typically lower due to the incomplete nature of most binding and release steps. Various embodiments of the invention can achieve ranges of enrichment factors having a lower limit of 1 and an upper limit of 10,000.

Sometimes in order to improve recovery it is desirable to pass the desorption solvent through the extraction bed multiple times, e.g., by repeatedly aspirating and discharge the desorption solvent through the extraction bed and lower end of the column. Step elutions can be performed to remove materials of interest in a sequential manner. Air may be introduced into the bed at this point (or at any other point in the procedure), but because of the need to control the movement of the liquid through the bed, it is not preferred.

The desorption solvent will vary depending upon the nature of the analyte and the extraction medium. For example, where the analyte is a his-tagged protein and the extraction medium is an IMAC resin, the desorption solution will contain imidazole or the like to release the protein from the resin. In some cases desorption is achieved by a change in pH or ionic strength, e.g., by using low pH or high ionic strength desorption solution. A suitable desorption solution can be arrived at using available knowledge by one of skill in the art.

Extraction columns and devices of the invention should be stored under conditions that preserve the integrity of the extraction medium. For example, columns containing agarose- or sepharose-based extraction media should be stored under cold conditions (e.g., 4 degrees Celsius) and in the presence of 0.01 percent sodium azide or 20 percent ethanol. Prior to extraction, a conditioning step may be employed. This step is to ensure that the tip is in a uniform ready condition, and can involve treating with a solvent and/or removing excess liquid from the bed. If agarose or similar gel materials are used, the bed should be kept fully hydrated before use. The bed could also be kept fully hydrated by coating or loading the bed with a high boiling solvent, such as glycerol.

Often it is desirable to automate the method of the invention. For that purpose, the subject invention provides a device for performing the method comprising a column containing a packed bed of extraction medium, a pump attached to one end of said column, and an automated means for actuating the pump.

The automated means for actuating the pump can be controlled by software. This software controls the pump, and can be programmed to introduce desired liquids into a column, as well as to evacuating the liquid by the positive introduction of gas into the column if so desired.

Multiplexing

In some embodiments of the invention a plurality of two-step purifications are run in a parallel fashion, e.g., multiplexed. This allows for the simultaneous, parallel processing of multiple samples.

Multiplexing can be accomplished, for example, by arranging the columns in parallel so that fluid can be passed through them concurrently. When a pump is used to manipulate fluids through the column, each column in the multiplex array can have its own pump, e.g., syringe pumps activated by a common actuator. In certain embodiments, pipette tip columns are attached to a multi-channel pipette. Alternatively, columns can be connected to a common pump, a common vacuum device, or the like. In another example of a multiplex arrangement, the plurality of columns is arranged in a manner such that they can be centrifuged, with fluid being driven through the columns by centrifugal force. Multiplexing is described in more detail in published U.S. Patent Application 20050019950 which is incorporated by reference herein.

A liquid handling system can be used in those embodiments in which multiple samples are processed simultaneously. The MEA™ personal purification system (PhyNexus, Inc.) works well for parallel sample processing. Other liquid handling systems can also be used. Examples of suitable systems include those commercially available from Zymark (e.g., the SciClone sample handler), Tecan (e.g., the Genesis NPS, Aquarius or TeMo) or Cartesian Dispensing (e.g., the Honeybee benchtop system), Packard (e.g., the MiniTrak5, Evolution, Platetrack. or Apricot), Beckman (e.g., the FX-96), Matrix (e.g., the Plate Mate 2 or SerialMate) and others.

In some embodiments, the invention provides a multiplexed extraction system comprising a plurality of extraction columns of the invention, e.g., low dead volume pipet tip columns having small beds of packed gel resins. The system can be automated or manually operated. The system can include a pump or pump in operative engagement with the extraction columns, useful for pumping fluid through the columns in a multiplex fashion, i.e., concurrently. In some embodiments, each column is addressable. The term "addressable" refers to the ability of the fluid manipulation mechanism, e.g., the pumps, to individually address each column. An addressable column is one in which the flow of fluid through the column can be controlled independently from the flow through any other column which may be operated in parallel. In practice, this means that the pumping means in at least one of the extraction steps is in contact and control of each individual column independent of all the other columns. For example, when syringe pumps are used, i.e., pumps capable of manipulating fluid within the column by the application of positive or negative pressure, then separate syringes are used at each column, as opposed to a single vacuum attached to multiple syringes. Because the columns are addressable, a controlled amount of liquid can be accurately manipulated in each column. In a non-addressable system, such as where a single pump is applied to multiple columns, the liquid handling can be less precise. For example, if the back pressure differs between multiplexed columns, then the amount of liquid entering each column and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

In those embodiments where the extraction column is a pipette tip column, a plurality of pipette tip columns can be attached to a multi-channel pipettor. In certain embodiments the multi-channel pipettor is controlled by a controller which, in turn, is controlled by a computer program or software.

The invention also provides software for implementing the methods of the invention. For example, the software can be programmed to control manipulation of solutions and addressing of columns into sample vials, collection vials, for spotting or introduction into some analytical device for further processing.

The invention also includes kits comprising one or more reagents and/or articles for use in processes related to the instant invention, e.g., buffers, standards, solutions, columns, sample containers, etc.

Recovery of Native Proteins

In some embodiments, the extraction devices and methods of the invention are used to purify proteins that are functional, active and/or in their native state, i.e., non-denatured. This is accomplished by performing the extraction process under non-denaturing conditions. Non-denaturing conditions encompasses the entire protein extraction process, including the sample solution, the wash solution (if used), the desorption solution, the extraction phase, and the conditions under which the extraction is accomplished. General parameters that influence protein stability are well known in the art, and include temperature (usually lower temperatures are preferred), pH, ionic strength, the use of reducing agents, surfactants, elimination of protease activity, protection from physical shearing or disruption, radiation, etc. The particular conditions most suited for a particular protein, class of proteins, or protein-containing composition vary somewhat from protein to protein.

Analytical Techniques

Extraction columns and associated methods of the invention find particular utility in preparing samples of analyte for analysis or detection by a variety of analytical techniques. In particular, the methods are useful for purifying an analyte, class of analytes, aggregate of analytes, etc, from a biological sample, e.g., a biomolecule originating in a biological fluid. It is particularly useful for use with techniques that require small volumes of pure, concentrated analyte. In many cases, the results of these forms of analysis are improved by increasing analyte concentration. In some embodiments of the invention the analyte of interest is a protein, and the extraction serves to purify and concentrate the protein prior to analysis. The methods are particular suited for use with label-free detection methods or methods that require functional, native (i.e., non-denatured protein), but are generally useful for any protein or nucleic acid of interest.

In some embodiments, the systems and methods of the invention are useful for preparing protein samples for crystallization, particularly for use in X-ray crystallography-based protein structure determination. The invention is particularly suited for preparation of samples for use in connection with high throughput protein crystallization methods. These methods typically require small volumes of relatively concentrated and pure protein, e.g., on the order of 1 μL, per crystallization condition tested. Instrumentation and reagents for performing high throughput crystallization are available, for example, from Hampton Research Corp. (Aliso Viejo, Calif.), RoboDesign International Inc. (Carlsbad, Calif.), Genomic Solutions, Inc. (Ann Arbor, Mich.) and Corning Life Sciences (Kennebunk, Me.). Typically, protein crystallization involves mixing the protein with a mother liquor to form a protein drop, and then monitoring the drop to see if suitable crystals form, e.g., the sitting drop or hanging drop methods. Since the determination of appropriate crystallization conditions is still largely empirical, normally a protein is tested for crystallization under a large number of different conditions, e.g., a number of different candidate mother liquors are used. The protein can be purified by extraction prior to mixture with mother liquor. The sample can be collected in an intermediate holding vessel, from which it is then transferred to a well and mixed with mother liquor. Alternatively, the protein drop can be dispensed directly from the column to a well. The invention is particularly suited for use in a high-throughput mode, where drops of protein sample are introduced into a number of wells, e.g., the wells of a multi-well plate (e.g., 94, 384 wells, etc.) such as a CrystalEX 384 plate from Corning (Corning Life Sciences, Kennebunk Me.). The protein drops and/or mother liquors can be dispensed into microwells using a high precision liquid dispensing system such as the Cartesian. Dispensing System Honeybee (Genomic Solutions, Inc., Ann Arbor, Mich.). In high throughput modes it is desirable to automate the process of crystals trial analysis, using for example a high throughput crystal imager such as the RoboMicroscope III (RoboDesign International Inc., Carlsbad, Calif.).

Other analytical techniques particularly suited for use in conjunction with certain embodiments of the invention include surface immobilized assays, immunological assays, various ligand displacement/competition assays, direct genetic tests, biophysical methods, direct force measurements, NMR, electron microscopy (including cryo-EM), microcalorimetry, mass spectroscopy, IR and other methods such as those discussed in the context of binding detection chips, but which can also be used in non-chips contexts.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. The instrument used in all the following examples that follow is the MEA Personal Purification System (PhyNexus, Inc., San Jose, Calif.). They should not be construed as limiting the scope of the invention, but merely as being illustrative and representative thereof.

Example 1

Purification with IMAC

Protein Yield and Concentration as a Function of Starting Concentration of a Pure Protein PhyTip IMAC 200+ columns with 5 ul bed (lot 812) were used for this experiment. Twelve columns were loaded with $His_6$-ubiquitin (>95% pure, Boston Biochem) samples in 180 μl of capture buffer (10 mM $NaH_2PO_4$, 5 mM imidazole, 0.3 M NaCl, pH 7.4) containing 5 mM imidazole. Four different amounts of his ubiquitin were used: 3×100 μg, 3×200 μg, 3×250 μg, 3×300 μg. Capture was performed using 10 cycles at a flow rate of 250 μl/min. Two washes were performed each was one cycle at 100 μl/min. The first wash was 200 μl of 20 mM imidazole in PBS and the second wash was 200 μl water. Following capture, the ubiquitin was eluted from the column with 10 ul of 50 mM imidazole in PBS using 4 cycles with a flow rate of 100 μl/min. Following elution, the sample is diluted with water to a final volume of 100 μl. 10 μl of the above sample was diluted with another 50 μl of water before being analyzed by HPLC using a non-porous two-micron polymer reverse phase column, with TFA ion pairing reagent and an ACN gradient at 80° C. The injection volume was 40 μl.

As the amount of protein loaded on the column increases, the concentration of eluted ubiquitin also increases (FIG. 1). However, the % yield decreases as the starting amount of protein increases. This experiment shows it is possible to obtain concentrations upwards of 10 mg/ml using these conditions.

Example 2

Two-Step Purification Using IMAC

Twelve PhyTip IMAC 1000+ columns with a 20 ul bed (Ni-NTA lot 880, Ni-Sepharose lot 881) were used for this experiment. Six columns of each type were loaded with 650 µg of His$_6$-ubiquitin (>95% pure, Boston Biochem) samples in 500 µl of capture buffer (10 mM NaH$_2$PO$_4$, 5 mM imidazole, 0.3 M NaCl, pH 7.4) containing 5 mM imidazole. Capture was performed using 10 cycles at a flow rate of 250 µl/min. Two washes were performed. Each wash was one cycle at 250 µl/min. The first wash was 600 µl of 20 mM imidazole in PBS and the second wash was 600 µl water. Two different buffers were used to elute the His$_6$-ubiquitin. Three Ni-NTA columns and three Ni-Sepharose columns were eluted with 60 µl of 300 mM PO$_4$, 100 mM NaCl. The other six tips were eluted with 300 mM citrate, 50 mM NaCl. One tip of each type and each condition are set aside as a control. The elution products were neutralized to separately with saturated NaHCO$_3$ to a pH of approximately 7.5.

The neutralized samples then taken up in an IMAC 200+ PhyTip with a 5 µl bed (10 cycles at 250 µl/min) and washed once with water. The columns were eluted with 10 µl of 500 mM imidazole. All samples were diluted in water to a final volume of 100 ul. 10 ul of each sample was diluted with another 50 ul of water and then analyzed by HPLC using a non-porous two-micron polymer reverse phase column, with TFA ion pairing reagent and an ACN gradient at 80° C. The injection volume was 40 µl.

Figure 2:
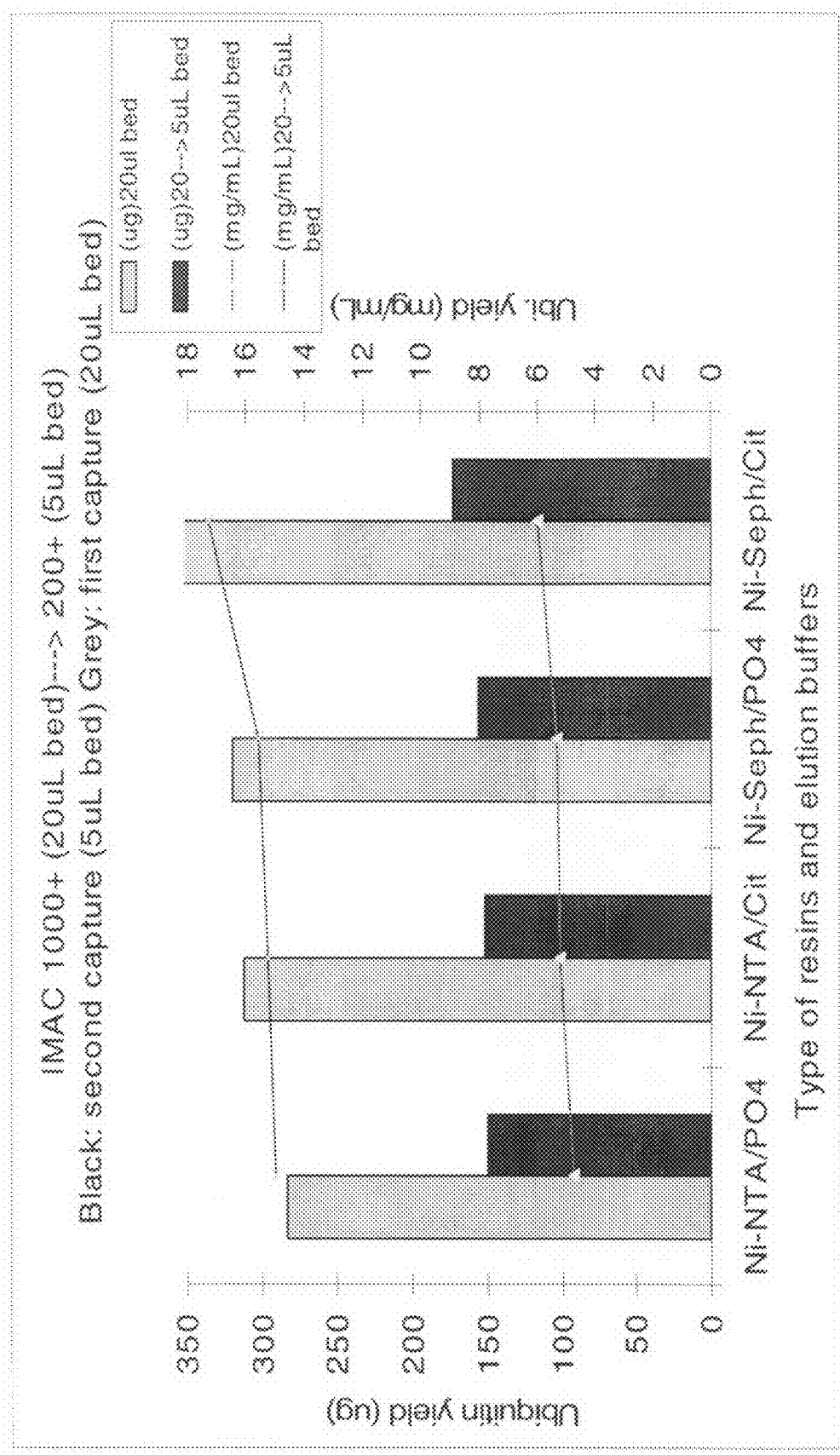
FIG. 2 is a graph of a two-step purification procedure using different column media and elution buffers.

The highest concentration of purified ubiquitin was obtained using the Ni-Sepharose column and eluting with citrate (FIG. 2) however all four combinations of resins and elution buffers yielded very high concentrations of purified ubiquitin.

Example 3

IMAC 200+ PhyTip; Different Imidazole Concentrations in Wash and Elution Buffers In this experiment two different proteins were purified using IMAC 200+ PhyTip columns and protein yield as a function of imidazole concentration in the wash and elution buffers was examined. Two different proteins were purified; a his-tagged DNA binding protein (Pho) in a bacterial lysate (Univ. of Sheffield, Sheffield, UK) and His$_6$-ubiquitin (>95% pure, Boston Biochem). Twelve IMAC 200+ tips (lot 809) were used for each protein. The lyophilized Pho lysate was re-suspended in 0.5 ml and divided into 15 aliquots and added to IMAC capture buffer to make a total volume of 180 µl. 20 µg of His$_6$-ubiquitin was dissolved in 180 µL of IMAC capture buffer. Capture was performed using 5 cycles at a flow rate of 100 µL/min. Two washes were performed, each with 2 cycles at a flow rate of 100 µL/min. The first wash was 200 µL of [5 or 20 mM] imidazole in 250 mM NaCl-PBS and the second wash was 200 µL of water).

The trapped proteins were eluted with 20 µL of imidazole in 10 mM phosphate at pH 7.2, 140 mM NaCl Five different concentrations of imidazole were compared: 100 mM, 200 mM, 250 mM, 300 mM, 400 mM, and 500 mM. The elution was performed with four cycles at the flow rate of 100 µL/minute. The eluted sample was diluted with water (40 µL) and analyzed by HPLC using a non-porous two-micron polymer reverse phase column, with TFA ion pairing reagent and an ACN gradient at 80° C. The injection volume was 40 µl.

FIG. 3 indicates the IMAC affinity for the two different proteins. His-Ubiquitin yield is insensitive to the change of imidazole concentration in the wash buffer (FIG. 3A) while the yield of "Pho" protein decreased approximately 50% by increasing the imidazole wash concentration from 5 mM to 20 mM (FIG. 3B)

In terms of elution buffer, the yield of "Pho" protein concentration leveled off after an imidazole concentration of 250-300 mM (FIG. 3B). But the yield of His-Ubiquitin continued to increase as the concentration of imidazole was increased from 100 mM to 500 mM.

The above mentioned differences between His-Ubiquitin and "Pho" protein suggest that His-Ubiquitin binds to the IMAC surface much more tightly, and thus is insensitive to change in the low concentrations of imidazole in the washes and requires a much higher concentration of imidazole in the elution buffer.

This study suggests it is necessary to optimize the PhyTip purification for each protein in order to achieve the highest possible yield at the best purity.

Example 4

Effect of the Number of Capture Cycles on Protein Recovery

Fluorescent GST-ubiquitin was prepared as follows: GST-ubiquitin (Boston Biochem) was diluted to a concentration of 1 mg/ml in PBS. GST-ubiquitin (0.5 mg) was added to Alexa488-NHS vial (component of Alexa 488 Protein Labeling Kit from Molecular Probes, Inc.) and incubated for one hour at room temp with mixing via magnetic stir bar. While the labeling reaction was incubating, a PD-10 gel filtration desalting column (Amersham Biosciences) was equilibrated with 25 ml PBS at room temperature. The labeling reaction was added to PD-10 gel filtration desalting column and the column was washed with PBS. The first 2.5 mL was discarded and the next three 1 ml fractions were collected and pooled together. Protein quantitation was performed using the BCA Assay (Pierce) to measure the concentration of protein in the final product of the labeling reaction after gel filtration.

The protein was diluted to 1 µg/ml in 10 mM NaH$_2$PO$_4$, 150 mM NaCl, pH 7.4, 1% Triton X-100 and 10 mg/ml BSA and distributed among thirteen 200 µl aliquots.

One of the aliquots was retained as the "input" sample. The remaining twelve aliquots were loaded onto separate 200+ PhyTip glutathione columns containing 5 µl bed (PhyNexus). Capture was controlled using the ME-100 syringe controller set to a flow rate of 250 µl/min. Three replicate samples were loaded with each of four different number of capture cycles (2, 4, 8, and 20 cycles).

Figure 4:
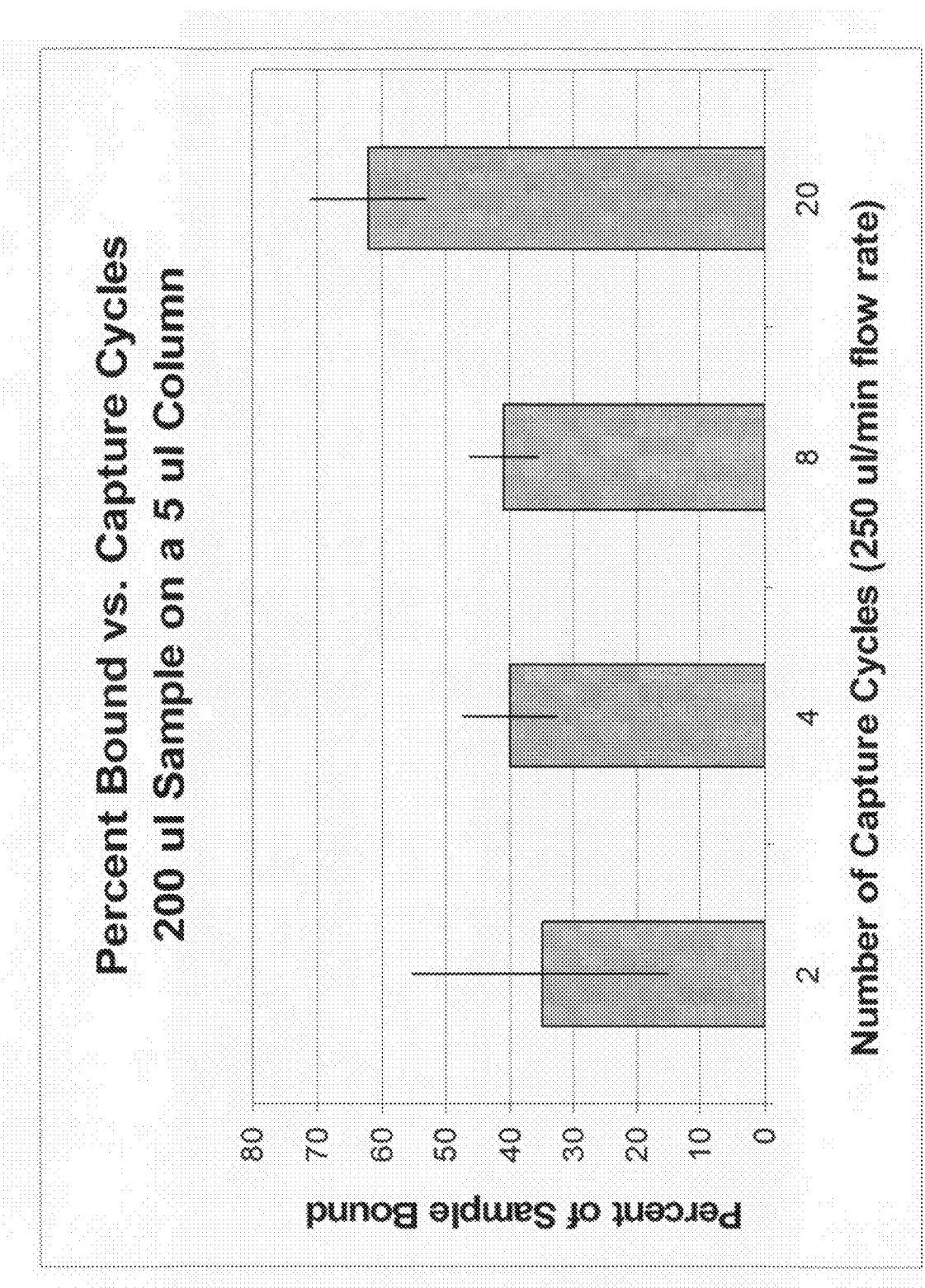
FIG. 4 is a graph showing the effect of varying the number of capture cycles on % recovery of GST-ubiquitin.

The fluorescence of all thirteen samples was measured with an SPEX FluoroMax-3 fluorometer using excitation 488 nm and emission of 515 nm. The setting for the instrument was calibrated to a sensitivity level that provided a linear response between 0.1 to 100 µg/ml using a dilution series of the Alexa488 labeled GST-ubiquitin. The percent bound was calculated by comparing the fluorescence intensity resulting after loading onto the columns against the intensity of the untreated "input" sample (FIG. 4). The greatest sample capture (approximately 62%) was obtained using 20 capture cycles which was significantly higher than the capture obtained from 8 (41%), 4 (40%), and 2 (35%) capture cycles.

Example 5

Protein Recovery Versus Number of Capture Cycles Using a PhyTip 200+ Protein A 5 µL Bed Column The number of capture cycles and the capture flow rate versus IgG yield were explored. To compensate for experimental variations, each condition was applied to two different pipette tip columns. Materials used were mouse IgG$_2$a (Fitzgerald, PN 10-F50), capture buffer (10 mM PO4, 140 mM NaCl @ pH 7.4) and phosphate buffer.

IgG was dissolved in the capture buffer at 10 μg per 200 μL in the presence of 400 μg of BSA. Each Protein A PhyTip 200+ 5 μL bed (PhyNexus) column was processed with 200 μL of the appropriate sample from above using one, five, or ten cycles of loading at a flow-rate of 100, 250, 500 or 1000 μL/min using an ME 200 Purification System (PhyNexus, Inc., San Jose), and washed with 200 μL of the same capture buffer followed by 200 μL of water, both with one cycle at a flow-rate of 250 μL/min.

The trapped IgG was eluted with 60 μL of phosphate buffer (300 mM; pH 2.5). The eluted protein samples were analyzed by HPLC using a non-porous two-micron polymer reverse phase column, with TFA ion pairing reagent and an ACN gradient at 80° C. The injection volume was 40 μl.

Figure 5:
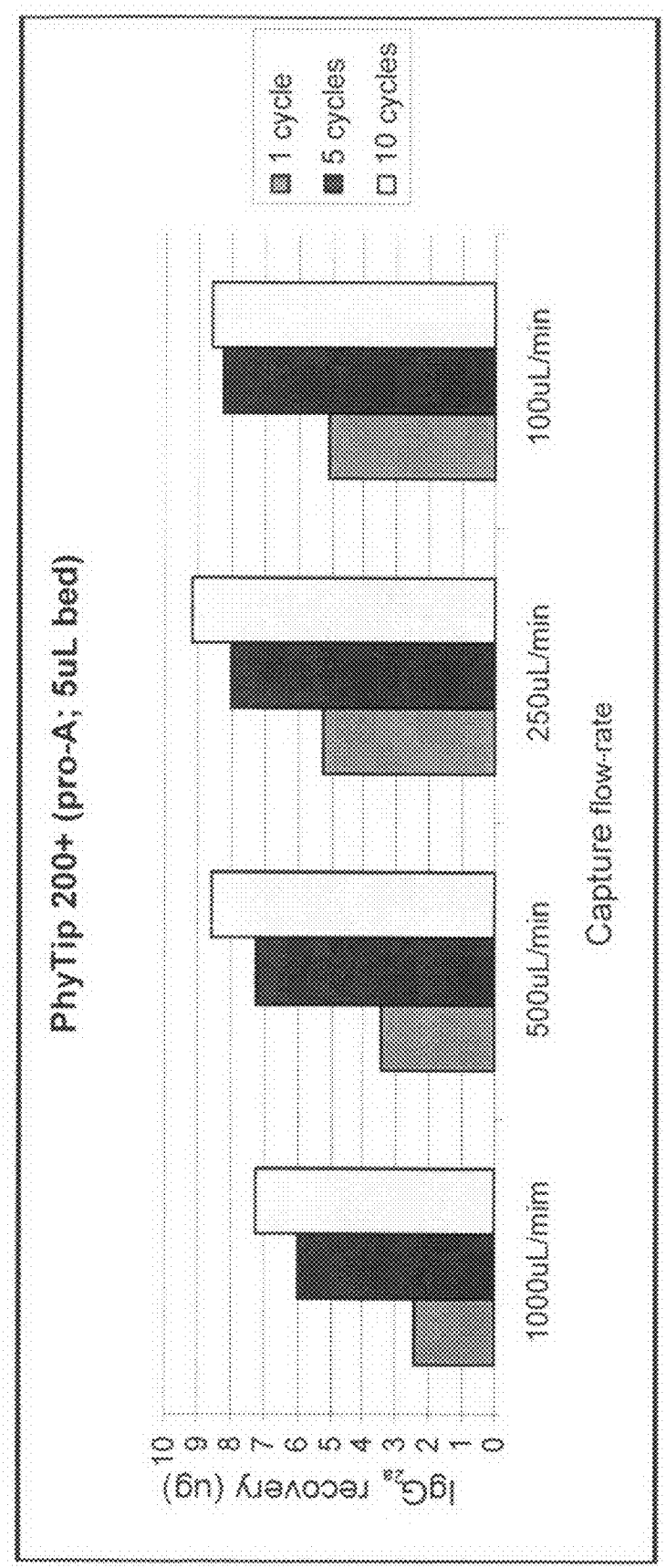
FIG. 5 is a graph showing the effect of varying the flow rate and number of capture cycles on IgG recovery.

The capture flow rate in combination with the number of capture cycles was examined. The flow rates of 0.10, 0.25, 0.50, and 1.00 mL/min were used in combination of one, five, and ten cycles of capture. Based on the data in FIG. 5, and as expected, slower capture flow rates provided higher yield at all three sets of capture cycles. At every flow rate, higher yields were attained by increasing the number of capture cycles. FIG. 5 provides a guideline for capture conditions depending on whether the objectives are maximum yield with no limitation on time or shortest run times with reasonable yield.

Flow rate and the number of capture cycles had a significant impact on the IgG capture efficiency. The IgG recovery increased rapidly from one to five capture cycles and improved further as the number of capture cycles increased to ten. However, the improvement in IgG yield was not as drastic as going from one to five.

Example 6

Automating Large-Volume Sample Processing with a Robotic System

Figure 6:
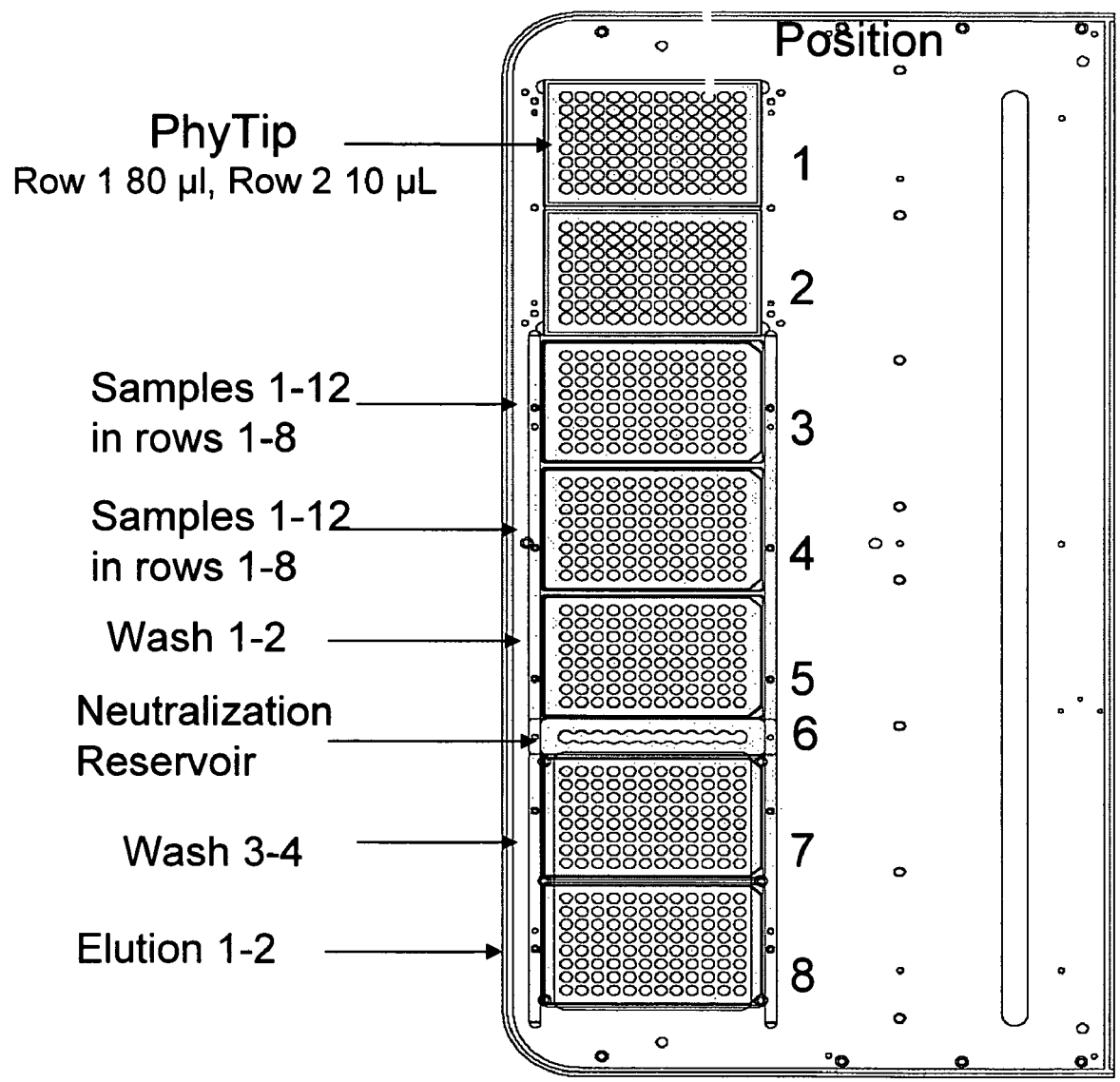
FIG. 6 depicts a configuration of the MEA Personal Purification System such that a total of 12 samples can be processed at a time.

The MEA Personal Purification System (PhyNexus, Inc.) is configured to purify twelve, large-volume samples (25 mL) in an automated manner. Each sample is an *E. coli* lysate containing a his-tagged protein of interest. FIG. 6 shows the deck of the MEA instrument. Positions 3 and 4 contain the samples in deep-well plates (2 mL wells, with approximately 1.5-1.6 mL per well). Each plate contains 12.5 ml of each sample Twelve IMAC 1000+ pipette tip columns (80 μL bed volume) are loaded onto the pipettor. The first row of samples is run through the columns for a total of four capture cycles at 1 mL/min. This process is repeated for the next seven rows so that 12.5 mL of a single sample is processed through twelve IMAC columns. Using the same pipette tips, the capture process is repeated on the supernatants from the plate in position 4. At this point, 25 ml of supernatant from each of the twelve samples has been loaded onto the PhyTip column.

Next, the IMAC tips are brought to the first wash (position 5) and 1 mL of wash solution (20 mM imidazole in PBS) is passed through the column for two wash cycles at 1 mL/min. For the second wash, PBS is passed through the column for two cycles at 1 mL/min. This is followed by an elution at position 8 using 150 μL of citric acid, 200 mM NaCl pH 2.5 using four cycles at 1 mL/min. Next a transfer tip is used to bring the pH to 7.4 using a 1 M sodium carbonate solution from the neutralization reservoir.

For the second step of the process, twelve IMAC 1000+ affinity pipette tip columns (10 μL bed volume) are automatically loaded onto the pipettor, and the samples eluted from the first IMAC columns are run through the columns for four capture cycles at 1 mL/min. Once completed, the IMAC columns are brought to the plate containing washes 3-4 (position 7), and 1 mL of 200 mM NaCl is passed through the column for two cycles at 1 mL/min. The saline wash is repeated and the columns are eluted (at position 8) with 30 μL of 500 mM imidazole.

With this configuration, a dual-stage IMAC/IMAC separation process can be performed for twelve, 25-mL samples with an automated MEA Personal Purification System.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

What is claimed is:

1. A method for purifying and concentrating a protein from a sample solution comprising the steps of:
    a) introducing the sample solution containing the protein into a first pipette tip column, wherein said first pipette tip column is comprised of a first packed bed of extraction medium, wherein the first packed bed of extraction medium is comprised of a functional group, and whereby at least some portion of the protein is adsorbed by the first packed bed of extraction medium;
    b) passing a wash solution through the first packed bed of extraction medium;
    c) passing a first desorption solvent through the first packed bed of extraction medium, whereby at least some fraction of the bound protein is desorbed from the first packed bed of extraction medium into the desorption solvent, and wherein, as a result of step (c), the protein is purified from other components in the sample solution;
    d) optionally adjusting the pH of the purified protein in the desorption solvent;
    e) introducing the purified protein into a second pipette tip column, wherein the second pipette tip column is comprised of a second packed bed of extraction medium, wherein the second packed bed of extraction medium is comprised of a functional group, wherein the functional group of the second packed bed of extraction medium is the same as the functional group of the first packed bed of extraction medium, wherein the capacity of the second pipette tip column has is in the range of 1% to 95% of the capacity of the first pipette tip column, and whereby at least some portion of the protein is adsorbed by the second packed bed of extraction medium;
    f) optionally passing a wash solution through the second packed bed of extraction medium; and
    g) passing a second desorption solvent through the second packed bed of extraction medium, whereby at least some fraction of the bound protein is desorbed from the second bed of extraction medium into the second desorption solvent, and wherein the purified protein has a concentration of at least 5 mg/ml.

2. The method of claim 1, wherein the first packed bed of extraction medium and the second packed bed of extraction medium are optionally comprised of a gel resin.

3. The method of claim 2 wherein the gel resin is an affinity resin.

4. The method of claim 3, wherein the affinity resin is agarose or sepharose.

5. The method of claim 4, wherein the affinity resin, wherein the functional group is selected from a group consisting of Protein A, Protein G, Protein L, and an immobilized metal.

6. The method of claim 1, wherein following step (g), the protein has a concentration of at least 10 mg/ml.

7. The method of claim 6, wherein following step (g), the protein has a concentration of at least 15 mg/ml.

8. The method of claim 1, wherein the first and second pipette tip columns are attached to a pipettor.

9. The method of claim 8 wherein the pipettor is further comprised of:
   a) a controller; and
   b) a computer, wherein said computer can be programmed to control the movement of the pipettor through the controller, thereby automating the method.

10. The method of claim 9 wherein a plurality of first pipette tip columns are used simultaneously.

11. The method of claim 10 wherein a plurality of second pipette tip columns are used simultaneously.

12. The method of claim 5, wherein following step (g), the protein has a concentration of at least 10 mg/ml.

13. The method of claim 12, wherein following step (g), the protein has a concentration of at least 15 mg/ml.

14. The method of claim 5, wherein the pipettor is further comprised of:
   a) a controller; and
   b) a computer, wherein said computer can be programmed to control the movement of the pipettor through the controller, thereby automating the method.

15. The method of claim 14, wherein a plurality of first pipette tip columns are used simultaneously and a plurality of second pipette tip columns are used simultaneously.

* * * * *